United States Patent [19]

Heikkilä et al.

[11] Patent Number: 5,998,607
[45] Date of Patent: Dec. 7, 1999

[54] METHOD FOR PRODUCING XYLITOL

[75] Inventors: Heikki Heikkilä; Outi Puuppo, both of Espoo; Matti Tylli, Kantvik; Hannele Nikander, Espoo; Johanna Nygrén, Virkkala; Mirja Lindroos, Kirkkonummi; Olli-Pekka Eroma, Kotka, all of Finland

[73] Assignee: Xyrofin Oy, Helsinki, Finland

[21] Appl. No.: 08/881,880

[22] Filed: Jun. 24, 1997

[30] Foreign Application Priority Data

Jun. 24, 1996 [FI] Finland .................................. 962610

[51] Int. Cl.$^6$ .............................. C07H 1/06; C07C 31/18
[52] U.S. Cl. ..................... 536/124; 536/127; 536/128; 568/852; 568/861
[58] Field of Search .................... 568/852, 861; 127/36, 40; 536/124, 127, 128

[56] References Cited

U.S. PATENT DOCUMENTS

| | | | |
|---|---|---|---|
| 3,586,537 | 6/1971 | Steiner et al. | 127/37 |
| 3,784,408 | 1/1974 | Jaffe et al. | 127/37 |
| 4,008,285 | 2/1977 | Melaja et al. | 260/635 C |
| 4,066,711 | 1/1978 | Melaja et al. | 260/637 R |
| 4,075,406 | 2/1978 | Melaja et al. | 536/1 |
| 4,631,129 | 12/1986 | Heikkila | 210/635 |
| 5,563,303 | 10/1996 | Vuorinen | 568/864 |
| 5,637,225 | 6/1997 | Heikkilä et al. | 210/659 |

FOREIGN PATENT DOCUMENTS

| | | |
|---|---|---|
| 0 694 515 A2 | 1/1996 | European Pat. Off. . |
| 78734 | 5/1989 | Finland . |
| WO 93/19030 | 9/1993 | WIPO . |
| WO 94/26380 | 11/1994 | WIPO . |
| WO 95/29002 | 11/1995 | WIPO . |
| WO 96/27028 | 9/1996 | WIPO . |

OTHER PUBLICATIONS

Härkönen, et al. (1980) "Hydrogenation of Xylose to Xylitol with Raney Nickel Catalyst", *Kemia–Kemi* 3: 98–100.

"Xylitol—An Effective Aid in Caries Prevention", Xylitol Information Bureau, 41–51 Brighton Rd., Redhill, Surrey RH1 6YS, United Kingdom, (1995).

*Primary Examiner*—Howard C. Lee
*Attorney, Agent, or Firm*—Scully, Scott, Murphy & Presser

[57] ABSTRACT

The invention relates to a method for producing xylitol from a material containing xylose and xylonic acid. According to the method, xylose and xylonic acid are separated from the material containing xylose and xylonic acid, whereafter the separated xylose and xylonic acid are reduced to xylitol, and the xylitol is recovered.

42 Claims, No Drawings

METHOD FOR PRODUCING XYLITOL

The invention relates to a method for producing xylitol from a material containing xylose and xylonic acid. Xylose and xylonic acid are found, for example, in the cooking liquor of a sulphite cook.

A sulphite cooking liquor can be obtained when a mass is produced with the sulphite method. A sulphite cooking liquor contains insoluble wood material, lignin, hexose and pentose sugars, organic acids and cooking chemicals. These cooking liquors were previously usually discharged into water systems. However, this has been recently prohibited by legislation concerning the environment and therefore methods for utilizing the sulphite cooking liquor have been developed. After the cooking, it is possible to evaporate and burn the sulphite cooking liquor to produce thermal energy, and the sulphur and base of the liquor can be returned to the cooking process. However, this procedure creates new environmental hazards due to the great sulphur content of the sulphite cooking liquor. Effective use requires that the sulphite cooking liquor is fractionated into its components.

In addition to xylose, the sulphite cooking liquor also contains xylonic acid that makes the separation of xylose from the liquor more difficult. However, it would be preferable that xylonic acid could be used as a raw material in the production of xylitol.

Xylitol is a naturally occurring sugar alcohol that is obtained through the reduction of xylose and that has sweetness corresponding to "normal sugar" but a calorie content (2.4 kcal/kg) lower than in normal sugar. Xylitol is found in small amounts in a variety of fruits and vegetables and it is also formed in the human body as a normal metabolic product. Due to certain metabolic, dental and technical properties, xylitol is a very good special sweetener for different purposes, such as chewing gum, sweets, confectionery, etc. It can be mentioned as an example that xylitol metabolism is independent of insulin metabolism and therefore diabetics can also use xylitol. Xylitol also slows down bowel movement and it may therefore be of use in diets. It has also been found out that xylitol does not cause dental caries but it might even have an anticariogenic effect.

Despite the numerous advantages of xylitol, its use has been rather limited. This is due to the relatively high price of xylitol, which in turn results from difficulties in producing xylitol on a larger scale.

Xylitol has been previously prepared from xylan-containing material through hydrolysis. This results in a monosaccharide mixture containing xylose, for example. Xylose is then reduced to xylitol through catalytic reduction (hydrogenation) usually in the presence of a nickel catalyst, such as Raney nickel. The literature of the art describes several methods for producing xylose and/or xylitol from xylan-containing material. Examples include U.S. Pat. No. 3,784,408 (Jaffe et al), U.S. Pat. No. 4,066,711 (Melaja et al), U.S. Pat. No. 4,075,406 (Melaja et al), U.S. Pat. No. 4,008,285 (Melaja et al) and U.S. Pat. No. 3,586,537 (Steiner et al).

In several plants, the majority of the hemicellulose is xylan that can be hydrolyzed into xylose. The primary starting material for xylan is the hemicellulose of deciduous trees that mainly consists of xylan. The use of xylan and xylose obtained as by-products of cellulose industry has recently also been the object of greater and greater attention. Xylose is formed, for example, in acid sulphite cookings where the typical bases include $Mg^{2+}$, $Ca^{2-}$, $NH_4^-$ and $Na^+$. The starting material may also be a cooking liquor of neutral sulphite cookings after the xylo-oligomers of xylan have been hydrolyzed. In the cooking liquors of acid sulphite cookings, the hemicelluloses are already in a monosaccharide form. The term "cooking liquor" refers in this connection to a solution used in cooking or obtained after the cooking, or part thereof. The known catalytic methods for reducing xylose used in the production of xylitol usually require that the xylose to be reduced does not contain harmful impurities. The purification is very demanding and requires a multistep process (see U.S. Pat. No. 4,631,129, Heikkilä, and PCT/FI95/00224, Heikkilä et al) for example since the catalysts used in the xylose reduction reaction are very sensitive to impurities (see Härkönen, M. and Nuojua, P., Kemia-Kemi, no 3 (1980) pp 98–100).

When a sulphite cooking liquor is used as a raw material for xylose, the problem is the variation in the cooking conditions. Depending on the conditions, hemicellulose of wood dissolves in different ways and produces greater or smaller amounts of xylose. In cooking conditions where only a small amount of xylose is produced, significant amounts of xylonic acid may also be formed. It is difficult to separate xylose found in such a product from a liquor containing xylonic acid for example by means of chromatography if the xylose is to be pure. The xylonic acid present in the solution makes the separation of xylose more difficult and therefore causes a decrease in the crystallization yield of xylose. However, it would be preferable to he able to use xylonic acid as a raw material for xylitol (see WO 93/1903, Vuorinen). The separation of xylose from a sulphite cooking liquor is known per se for example from WO 94/26380, Heikkilä et al, and WO 95/29002, Heikkilä et al.

The present invention relates to a method for producing xylitol from a material containing xylose and xylonic acid. The method is characterized in that xylonic acid is separated from the material containing xylose and xylonic acid, whereafter the separated xylonic acid is reduced. In a preferred embodiment of the invention, also xylose is separated. Xylose and xylonic acid are preferably separated chromatographically, by extraction, ion exchange or crystallization.

The material containing xylose and xylonic acid is preferably the cooking liquor of a sulphite cook, such as the cooking liquor of a magnesium sulphite cook. The production of xylose in the optimum manner chromatographically from a magnesium cooking liquor is restricted due to the fact that hardly any other cations except magnesium can be returned to the chemical circulation in the cellulose production. The chromatographic resins used in the process should preferably be in a magnesium ion form (Mg-ion separation), in which case the anions returned from the separation processes are magnesium salts. However, a separation resin used in a divalent form separates xylose less effectively than a separation resin in a monovalent form, see e.g. Finnish Patent 78,734 (Heikkilä). When the invention is applied, it is possible to use, instead of two successive magnesium-ion separations, one magnesium-ion separation and one sodium-ion separation between which there is a softening process where the magnesium ions are changed to sodium ions. The predominant cation in the fraction of the first separation is magnesium and it can be returned as such to the circulation of chemicals in the cellulose production. The residual fraction of the second separation cannot be returned to the circulation of the cellulose production (to the recovery of chemicals, energy production) since it contains foreign cations (=sodium). According to the invention, the entire residual fraction of the second separation is run through a cation exchanger in hydrogen form. The ionic strength of the fraction that is obtained from the second separation and that has been subjected to cation exchange corresponds to a relatively strong acid (low pH) after the ion exchange and therefore it can be used to regenerate to hydrogen form the cation-exchange resin used for softening the feed of the second separation. Simultaneously, the magnesium ions that have remained in the cation-exchange resin during the softening can be returned to the circulation of the cellulose production.

The resin used for the cation exchange of the residual fraction is mainly in sodium form after the ion exchange. This resin is regenerated with an acid back to the hydrogen form and the sodium that is discharged from the column at the beginning of the regeneration is returned to the softening column to bring it into the corresponding (=sodium) form (from the hydrogen form to which is was previously regenerated). The acid that is discharged at the beginning from the hydrogen-form softening column (sodium is changed to hydrogen) can be in turn used to regenerate to hydrogen form the resin used for the cation exchange of the residual fraction.

On the other hand, it has been found out that a two-step Mg—Mg separation can also be used advantageously for the separation of xylose and xylonic acid according to the invention. In the chromatographic $Mg^{2+}$ second separation of xylose carried out with a solution whose pH has not been adjusted (pH 1.5 to 2.5), xylonic acid is eluted almost simultaneously with xylose, which in turn reduces the purity of the xylose fraction. When the pH of the feed solution is increased with MgO to a pH value of about 3 or more, xylonic acid is eluted later, which increases the purity of the xylose fraction and the width of the xylose fraction. The pH can also be adjusted in the first separation steps but it is preferable to adjust it only in the second separation step as regards the consumption of chemicals.

The above disclosure concerning Mg separation also applies to the processing of a Ca-sulphite cooking liquor.

According to the invention, the separation is carried out suitably such that a) a cooking liquor of a magnesium sulphite cook is subjected to chromatographic separation by using a magnesium separation resin to obtain a fraction rich in xylose, a mixed fraction and a residual fraction in magnesium form, and b) the obtained fraction rich in xylose is chromatographed by using a separation resin that is in the form of magnesium or a monovalent metal, and a fraction concentrated with respect to xylose is recovered, and a fraction that is concentrated with respect to xylonic acid and that is in salt form is recovered.

When a separation resin that is in the form of a monovalent metal, preferably sodium, is used in step b), the xylose-containing fraction obtained in step a) is softened before step b). When the resin is in magnesium form in step b), the pH of the fraction obtained in step a) is adjusted preferably to a value of 3.0 to 6.5, especially 5.5.

The separation can also be carried out by extraction, preferably with ethanol, or by ion exchange or crystallization of Mg-xylonate.

It has turned out that separated xylose and xylonic acid can be reduced catalytically or by using metal hydride reagents, such as sodium borohydride. The reduction is carried out suitably catalytically, in which case preferred catalysts include Raney-type catalysts and noble-metal catalyst,, such as Ru, Pd, Rh and Pt, especially Ru.

A suitable reduction temperature in catalytic reduction is 70 to 150° C., preferably 100 to 130° C., and the reduction is carried out suitably at a pressure of 5000 to 20 000 kPa, preferably 10 000 to 13 000 kPa. The pH of the xylose to be reduced is preferably between 5 and 7 and the pH of xylonic acid is preferably between 1.5 and 2.5.

The xylose and xylonic acid fractions that have been separated before the reduction must be possibly purified, for example, by ion exchange The xylose and xylonic acid fractions may require further purification by neutralization/precipitation/filtration and/or treatment with carbon or an adsorbent. It is also possible to use two-step hydrogenation, which means that in the first step the hydrogenation is carried out for instance with a Raney nickel catalyst and in the second step with a noble-metal catalyst, for example. A manner of implementing the invention is to carry out preoxidation, in which case the separation of the xylonic acid concentrate from the solution becomes more effective. Xylitol prepared according to the invention can be preferably isolated from the product solution of the reduction chromatographically or preferably by crystallization.

The method according to the invention makes it possible to considerably reduce the costs of producing xylitol. The method enables for example better use of the raw material (the raw material is sufficient for as much as about twofold amount of xylitol).

The following examples illustrate the invention.

EXAMPLE 1

Mg-Na Separation

A sample obtained from a cooking liquor of a magnesium sulphite cook was chromatographed in a manner known per se (WO 94/26380) by using a strongly acid cation-exchange resin (polystyrene skeleton, activated by sulphonation) in magnesium form, to obtain a fraction rich in xylose, a mixed fraction and a magnesium-containing residual fraction that was returned to the preparation of the cooking acid of the magnesium sulphite cook. The fraction rich in xylose was softened or decationized by using a strong cation resin (DOW 88) that was in $H^+$ form and that had been regenerated with sulphuric acid. The temperature was 50° C. and the flow rate was 2 bulk volumes per hour. The refractometric dry solids content (RDS) of the feed was 20% by weight and the cycle length was about 0.6 kg of dry matter/0.5 1 of resin.

The pH of the obtained softened (decationized) syrup was adjusted to 5.5 with NaOH and the cations contained therein were mainly sodium ions and the syrup contained hardly any divalent cations. The syrup was chromatographed by using a strongly acid cation-exchange resin (Finex VO 9 C™) in sodium form, to obtain a fraction that was concentrated with respect to xylose and that was recovered, and a residual fraction in salt form (salt fraction) that contained a great amount of sodium. The amount of xylose in the feed fraction was 37.2% of the dry matter. The amount of xylose in the product fraction obtained after the separation was 55% of the dry matter and in the residual fraction 2% of the dry matter.

The salt fraction was decationized by using a strongly acid cation-exchange resin in $H^+$ form (DOW 88™). The flow rate was 2 bulk volumes per hour, the temperature was 50° C. and the dry solids content (RDS) of the feed was 5.6% by weight. The total cycle length was 7.2 1/l of resin. The pH of the decationized salt fraction was about 1 and it contained 0.252 $H^+$equivalents/l. The entire decationized salt fraction (7.2 l) was used to regenerate the softening resin (500 ml) containing mainly magnesium ions. The regeneration was carried out such that the acid fraction obtained at the beginning of the cycle and an additional acid were used to convert the softening resin in magnesium form into $H^+$ form. The Na-containing fraction of the decationiztion resin obtained at the beginning of the regeneration cycle was used to convert the softening resin into Na form. The capacities and cation contents of the resins at different stages of the softening and decationization are shown in Table 1.

TABLE 1

Resin analysis, ion forms at different stages of softening and decationization

|  | H (eq./l) | Na | K | Ca | Mg | Fe | Cations (eq./l) |
|---|---|---|---|---|---|---|---|
| Before softening of the second separation feed |  | 1.67 |  |  |  |  |  |
| After softening | 0.04 | 0 | 0.02 | 0.09 | 1.73 | 0 | 1.88 |
| Before decationization of the residue | 1.65 |  |  |  |  |  |  |
| After decationization of the residue |  | 1.74 | 0.02 | 0.11 | 0.02 | 0 | 1.89 |
| Before regeneration of the softening resin |  | 0 | 0.02 | 0.08 | 1.73 | 0 | 1.83 |
| After acid regeneration (acid added) | 1.67 |  |  |  |  |  |  |

EXAMPLE 2

Mg—Mg Separation

The second separation of Mg cooking liquor (step b)) was carried out in a chromatographic column with an $Mg^{2-}$ separation resin under the following conditions:

Separation resin: Finex V 11 C™, DVB⁻6.5%

Temperature: 65° C.

Flow rate: 0.9 m/h

* Sulphonated resin with polystyrene skeleton, cross-linked with divinyl benzene.

The xylose purity of the feed was 29.1% of the dry matter and the xylonic acid purity was 21.6% of the dry matter. Three fractions were recovered. The xylose purity of the xylose fraction was about 44% of the dry matter and the xylonic acid content of the xylonic acid fraction was about 41% of the dry matter. The order of elution of the recovered fractions was: salt, xylose, xylonic acid.

When the separation was carried out with a solution whose pH had not been adjusted (pH 2.1), the xylose fraction capacity was 5.2 kg of dry matter/h/m³. When the pH of the liquor was adjusted before the separation with MgO to a value of 3.5, 4.5, 5.3 and 6.5, the xylose capacity was 11.8, 10.7, 11.6 and 10.7 kg of dry matter/h/m³, respectively. When the pH of the separation was increased, a better separation result was obtained due to the stronger adherence of the xylonic acid to the resin.

EXAMPLE 3

Mg—Mg Separation

The second separation of the Mg cooking liquor according to Example 2 was carried out in a chromatographic column with a separation resin in $Mg^{2-}$ form under the conditions described in Example 2. The xylose and xylonic acid fractions then had the fraction purities disclosed in Table 2.

TABLE 2

Fraction purities obtained in separation II of the Mg cooking liquor

| pH | feed solution xylose % | % of dry matter xylonic acid % | xylose fraction xylose % | % of dry matter xylonic acid % | xylonic acid fraction xylose % | % of dry matter xylonic acid % |
|---|---|---|---|---|---|---|
| 2.1 | 29.1 | 21.6 | 44.0 | 29.9 | 39.9 | 41.8 |
| 3.5 | 26.1 | 19.8 | 44.0 | 18.8 | 8.2 | 44.6 |
| 4.5 | 26.7 | 19.4 | 44.0 | 13.9 | 10.6 | 40.8 |
| 5.3 | 27.7 | 19.8 | 44.0 | 11.4 | 11.1 | 41.5 |
| 5.5 | 34.0 | 35.0 | 52.0 | 34.0 | 2.0 | 76.0 |
| 6.5 | 26.3 | 18.9 | 44.0 | 13.6 | 8.8 | 39.5 |

EXAMPLE 4

Separation of Xylose and Xylonic Acid From Ca-Sulphite Cooking Liquor by Ethanol Extraction Commercially available dry and powdery Ca-sulphite cooking liquor of a deciduous tree, the composition of which is shown in Table 3 (1), was extracted with ethanol. The amount of powder in the extraction was 1500 g and the amount of 95% ethanol was 15 l. The mixture was mixed at 50° C. for 4 hours, whereafter it was filtered and the obtained cake was dried. The amount of the dissolved solids was 32%. The filtrate was evaporated in a rotavapor at a decreased pressure. The evaporation residue was dissolved in about 8 litres of water. The composition of the solution is shown in Table 3 (2) The xylose yield was about 78% and the xylonic acid yield was about 43%. The yields increased to 95% and 56%, respectively, when the ethanol extraction was repeated.

EXAMPLE 5

TABLE 3

Separation of xylose and xylonic acid by ethanol extraction

|  |  | 1 | 2 |
|---|---|---|---|
| Dry solids content | (g/100 g)* | 96 | 21 |
| Neutral oligo-saccharides | (% of dry matter) | 1.1 | 2.6 |
| Glucose | (% of dry matter) | 1.5 | 2.8 |
| Xylose | (% of dry matter) | 12.5 | 24.1 |
| Galactose-rhamnose | (% of dry matter) | 1.6 | 3.0 |
| Mannose | (% of dry matter) | 1.1 | 1.9 |
| Xylonic acid | (% of dry matter) | 5.2 | 5.4 |

*The dry solids content of the powder was determined with the K. Fischer method and the dry solids content of the solution was determined refractometrically by utilizing the refractive index table for pure xylose.

Oxidation of Xylose into Xylonic Acid 3.6 g of MgO, 6 g of xylose and 200 g of $SO_2$ solution (concentration 70 to 71 g $SO_2$/l) were added into autoclaves. The autoclaves were closed and put into a glycerol bath at 150° C. The autoclaves were kept in the bath for 1 h, 2 h, 4 h and 6 h, whereafter they were cooled. The solution was filtered and analyzed. 67% of the xylose was oxidized into xylonic acid in two hours.

TABLE 4

Oxidation of xylose into xylonic acid

| Time | Xylose g/l | Xylonic acid g/l |
|---|---|---|
| 0 | 30.0 | 0 |
| 1 | 8.8 | 16.8 |
| 2 | 4.2 | 20.1 |
| 4 | 2.8 | 17 |
| 6 | 1 | 16.5 |

EXAMPLE 6

Crystallization of Mg-Xylonate From Water

The starting solution was a xylonic acid fraction separated from Mg-sulphite cooking liquor. The xylonic acid fraction was crystallized at 10° C. and the mother liquor was separated by decantation. The Mg-xylonate crystal mass (dry matter 56.2%, purity 58.5% calculated on dry matter of xylonic acid) was crystallized from an ethanol-water solution in a ratio of 120 g of crystal mass/1 l of ethanol. The crystals were dried at room temperature. The purity of the Mg-xylonate crystals was 80.9% calculated on dry matter of xylonic acid. The crystals were dissolved in water into a solution of about 50%. Colour was removed from the solution by using carbon and a filter aid.

The magnesium xylonate solution (2040 g; dry solids content 45.8k (Karl-Fischer); xylonic acid purity 79.3% of dry flatter) was transferred to a 2-litre vessel (feed solution), where the Mg-xylonate was crystallized in the following manner.

The mass ($T_{mass}$ 57° C.) was seeded with 1 ml of Mg-xylonate solution. One hour after the seeding, a linear 70-hour cooling program (60° C. to 20° C.) was activated. After the linear cooling program, the Mg-xylonate was kept at a constant temperature (20° C.) for 72 hours. The crystals were filtered and washed with ethanol. The crystals were dried at 45° C. The yield was 337 g. The xylonic acid purity of the crystals was 94.3% on dry matter basis.

EXAMPLE 7

Crystallization of Mg-Xylonate From Water

The starting solution was a xylonic acid fraction separated from Mg-sulphite cooking liquor. The xylonic acid fraction was crystallized at 10° C. and the mother liquor was separated through decantation. The Mg-xylonate crystal mass was crystallized from the ethanol-water solution in a ratio of 120 to 150 g of crystal mass/1 l of ethanol. The crystals were dried at room temperature. The purity of the Mg-xylonate crystals was 80 to 94% calculated on dry matter of xylonic acid. The crystals were dissolved in water into a solution of about 35% having xylonic acid purity of 71%.

18.4kg of magnesium xylonate solution (RDS 34.3%) was used as a feed solution. Water was evaporated from the solution ($T_{mass}$ 40 to 55° C.). When the RDS of the mass reached 52.8%, the mass was transferred to a 6-litre cooling crystallizer (7.1 kg). 30 minutes later the mass was seeded with 0.7 g of Mg-xylonate crystals at 63° C. One hour after the seeding a linear 70-hour cooling program (60 to 20° C.) was activated. The mass having xylonic acid purity of 72.8% on dry matter basis and a dry solids content of 47.9% (Karl-Fischer) was centrifuged at 4500 rpm for 5 minutes and dried at 45° C. The yield was 1285 g of crystals. The xylonic acid purity of the Mg-xylonate crystals was 90.2% on dry matter basis.

EXAMPLE 8

Crystallization of Mg-Xylonate From Water

The starting solution was a xylonic acid fraction separated from Mg-sulphite cooking liquor.

20.6 kg of a magnesium xylonate solution (RDS 40.8%) was used as a feed solution. Water was evaporated from the solution ($T_{mass}$ 40 to 55° C.). When the RDS of the mass reached 59.5%, spontaneous crystallization occurred. The mass was transferred to a 10-litre crystallizer. After 15 minutes a linear 18-hour cooling program (60 to 20° C.) was activated. The mass having xylonic acid purity of 74.2% on dry matter basis and a dry solids content of 51.5% (Karl-Fischer) was centrifuged at 4500 rpm for 5 minutes, washed and dried at 45° C. The yield was 3.4 kg of crystals. The xylonic acid purity of the Mg-xylonate crystals was 82.5% on dry matter basis.

EXAMPLE 9

Adsorption of Xylonic Acid to a Slightly Basic Anion-Exchange Resin

The feed solution was a xylose fraction of the first separation according to Example 1 from the chromatographic separation process of Mg-sulphite cooking liquor. The fraction was supplied to a series of ion exchangers comprising a strongly acid cation-exchange resin (DOW 88™) and two slightly basic anion-exchange resins (DOW 66™) Cations adhere to the cation-exchange resin and xylonic acid is liberated from its salt, i.e. it is converted into a free acid, whereafter the anions adhere to the anion-exchange resin.

The dry solids content of the feed solution was 32%, the temperature was 40° C. and the flow rate was 2 bv/h/column (bv=bulk volume). In this experiment, the solution was treated in an amount approximately corresponding to the total resin volume.

In such a run, xylonic acid adhered to both anion-exchange resins: 22 g/l of resin to the first one and 63 g/l of resin to the second one. The feed and product analyses are shown in Table 5.

TABLE 5

Adsorption of xylonic acid

| | Xylose % dry matter | Xylonic acid % dry matter |
|---|---|---|
| Feed | 49.4 | 17.9 |
| Product | 75.2 | 4.8 |

EXAMPLE 10

Separation of Xylose by Using a Slightly Acid Cation-Exchange Resin

Chromatographic separation of Mg-sulphite cooking liquor was carried out by using a slightly acid cation-exchange resin, Finex CA 24 GC™. The temperature was 65° C. and the flow rate was 0.19 m/h. The pH of the feed solution was 1.2 and the xylose content was 9.8%. The xylose fraction capacity with the fraction purity of 25% was 9.6 kg of dry matter/m³/h and the maximum purity of xylose in the separation was 31.4%. The xylonic acid content in the feed solution was 5.5%/dry matter (RDS) and in the xylose fraction 16.7%/dry matter. The order of elution was: majority of the salt followed by xylose and xylonic acid almost simultaneously (xylonic acid slightly later).

EXAMPLE 11

Separation of Xylose by Using a Slightly Acid Cation-Exchange Resin

Chromatographic separation of Mg-sulphite cooking liquor was carried out by using a slightly acid cation-exchange resin, Purolite C 105™. The temperature was 65° C. and the flow rate was 0.7 m/h. The pH of the feed solution was 4.5 and the xylose content was 10.9%. The xylose fraction capacity with the fraction purity of 25% was 19.0 kg of dry matter/$m^3$/h and with the fraction purity of 40% it was 7.8 kg of dry matter/$m^3$/h and the maximum purity of xylose in the separation was 42.7%. The xylonic acid content in the feed solution was 5.6%/dry matter (RDS). The xylonic acid purity in the xylose fraction having fraction purity of 25%/dry matter of xylose was 11.7%/dry matter, and in the xylose fraction having fraction purity of 40%/dry matter of xylose the xylonic acid purity was 18.5%/dry matter. The salts, xylose and xylonic acid were eluted almost simultaneously (xylonic acid slightly later).

EXAMPLE 12

Separation of Xylose by Using a Fibre-Like Cation-Exchange Resin

Chromatographic separation of Mg-sulphite cooking liquor was carried out by using a fibre-like (staple fibre) cation-exchange resin, Smoptec 101,3™, polystyrene skeleton, that is activated with sulphonic acid. The temperature was 65° C. and the flow rate was 1.8 m/h. The pH of the feed solution was 2.2 and the xylose content was 8.9%. The maximum purity of xylose in the separation was 23.4%. The xylonic acid content in the feed solution was 5.1%/dry matter (RDS) and the maximum purity in the xylose fraction was 15.0%/dry matter. The order of elution was: majority of the salt, and xylose and xylonic acid together.

EXAMPLE 13

Separation of Xylose by Using a Strongly Acid Cation-Exchange Resin

Chromatographic separation of Mg-sulphite cooking liquor was carried out by using a strongly acid cation-exchange resin, Finex CS 11 GC™. The temperature was 65° C. and the flow rate was 0.7 m/h. The pH of the feed solution was 1.0 and the xylose content was 11.9%. The xylose fraction capacity with the fraction purity of 40% was 11.2 kg of dry matter/$m^3$/h and the maximum purity of xylose in the separation was 44.8%. The xylonic acid content in the feed solution was 5.5%/dry matter (RDS) and in the xylose fraction 25%/dry matter. The order of elution was: salt, xylose and xylonic acid. The two latter fractions partly overlapped.

EXAMPLE 14

Oxidation of Xylose 2 g of MgO, 62 g of Mg-sulphite cooking liquor and 140 g of $SO_2$ solution (concentration 70 to 72 g $SO_2$/l) were added into autoclaves. The autoclaves were closed and put into a glycerol bath at 150° C. The autoclaves were kept in the bath for 30 min, 1 h, 2 h and 4 h, whereafter they were cooled. The solution was filtered and analyzed. 28% of the xylose was oxidized into xylonic acid in four hours.

TABLE 6

Oxidation of xylose into xylonic acid

| Time | Xylose g/l | Xylonic acid g/l |
|---|---|---|
| 0 | 20.1 | 10.0 |
| 30 min | 15.8 | 10.7 |
| 1 h | 11.7 | 13.9 |
| 2 h | 7.7 | 15.7 |
| 4 h | 5.7 | 15.4 |

EXAMPLE 15

Hydrogenation of Xylonic Acid

The raw material was a xylonic acid fraction which was prepared as described in Examples 6, 7 and 8 and from which magnesium had been removed by cation exchange.

The hydrogenation was carried out in a 5-litre Medimex autoclave (batch-type reactor) at 110° C. and at a pressure of 13 000 kPa by using as a catalyst Ru/carbon (5% Ru on carbon, Engelhard CP 56xL/R/WW) the dosage of which was 18% of the dry matter. The time of hydrogenation was 3 hours. Table 7 shows the compositions of the starting material and the obtained product.

TABLE 7

Hydrogenation of xylonic acid

| | Composition of starting material (%/dry matter) | Composition of product (%/dry matter) |
|---|---|---|
| Xylonic acid | 94.2 | 8.3 |
| Xylitol | 0 | 75.9 |
| Arabinitol | 0 | 6.6 |
| Xylose | 1.1 | 0 |

EXAMPLE 16

Reduction with Sodium Borohydride of an Oxidized Xylose-Xylonic Acid Fraction Produced by Chromatographic Separation The reaction was carried out at a normal pressure and at room temperature by mixing. The reaction time was 2 hours after the addition of the reagent (added gradually). The fraction was reduced as such and after cation exchange at a dry solids content of about 10%. Sodium borohydride was added in the ratio of 3 g/100 g of the natural weight of the solution (=10 g of dry matter). The sodium borohydride was added in the form of 4% aqueous solution. The reaction was terminated with 6 N hydrochloric acid by acidifying the solution (pH 2). The results are shown in Table 8.

TABLE 8

Reduction of an oxidized xylose-xylonic acid fraction with sodium borohydride

|  | xylose (%/dry matter) | acid (%/dry matter) | xylitol (%/dry matter) |
|---|---|---|---|
| Acid fraction | 1.7 | 7.5 | 0 |
| Reduced acid fraction | 0.2 | 3.1 | 2.1 |
| Acid fraction + cation exchange | 1.9 | 8.1 | 0 |
| Reduced fraction + cation exchange | 0.6 | 3.2 | 2.4 |

EXAMPLE 17

Hydrogenation with Raney Nickel of a Mixture Concentrated with Respect to Xylonic Acid 166 g/l of xylonic acid in 70% methanol was hydrogenated in an autoclave with Raney nickel (2 g) at 122° C. and at a pressure of 6500 kPa for 18 hours. The results are shown in Table 9.

TABLE 9

Hydrogenation of a mixture concentrated with respect to xylonic acid

|  | Composition of starting material (%/dry matter) | Composition of product (%/dry matter) |
|---|---|---|
| Xylonic acid | 94.2 | 63.8 |
| Xylose | 1.1 | 0 |
| Xylitol | 0 | 15.0 |

EXAMPLE 18

Hydrogenation With Rhodium of a Mixture Concentrated With Respect to Xylonic Acid 166 g/l of xylonic acid in water was hydrogenated in an autoclaves by using as a catalyst 0.17 g of 5% Rh/2% Mo/Al$_2$O$_3$ at 140° C. and at a pressure of 6500 kPa for 18 hours. The results are shown in Table 10.

TABLE 10

Hydrogenation of a mixture concentrated with respect to xylonic acid

|  | Composition of starting material (%/dry matter) | Composition of product (%/dry matter) |
|---|---|---|
| Xylonic acid | 94.2 | 18.7 |
| Xylose | 1.1 | 0 |
| Xylitol | 0 | 53.1 |

EXAMPLE 19

Crystallization of Xylitol

The raw material was xylitol prepared as described in Examples 15 to 18.

97 g of xylitol (RDS 11.4%, feed solution) was evaporated into an RDS content of 91.4% at 60° C. The mass was transferred to a 1-litre reaction vessel where it was seeded with 0.06 g of xylitol crystals at 60° C. A linear 49-hour cooling program (60.5° C. to 30° C.) was activated. After the cooling, the temperature of the mass was increased by about 3° C. and the mass was centrifuged. The xylitol purity of the mass was 77% on the dry matter. The crystals were separated with a centrifuge (basket diameter 22 cm, mesh size 0.15 mm) at 4500 rpm for 5 minutes, and the crystals were washed. The yield was 30 g of dried crystals. The xylitol purity of the crystals was 81.2% on dry matter basis.

EXAMPLE 20

Crystallization of Xylitol

The raw material was xylitol prepared as described in Examples 15 to 18.

The xylitol solution was filtered through a membrane of 12 μm. 170 g (dry matter) of xylitol (RDS 19.7%, feed solution) was evaporated into an RDS content of 91.3% at 60° C. The mass was transferred to a 1-litre reaction vessel where it was seceded with 0.05 g of xylitol crystals at 60° C. A linear 41-hour cooling program (60.5° C. to 30° C.) was activated. After the cooling, the temperature of the mass was increased by about 3° C. and the mass was centrifuged. The xylitol purity of the mass was 64.3% of the dry matter. The crystals were separated with a centrifuge (basket diameter 22 cm, mesh size 0.15 mm) at 4500 rpm for 5 minutes and washed. The yield was 54 g of dried crystals. The xylitol purity of the crystals was 93.3% on dry matter basis.

EXAMPLE 21

Crystallization of Xylitol

The raw material was xylitol prepared as described in Examples 15 to 18.

The xylitol solution was filtered through a membrane of 12 μm. 185 g (dry matter) of xylitol (RDS 20.9%, feed solution) was evaporated into an RDS content of 92.2% at 60° C. The mass was transferred to a 1-litre reaction vessel where it was seeded with 0.05 g of xylitol crystals at 56.5° C. A linear 69-hour cooling program (57° C. to 30° C.) was activated. After the cooling, the temperature of the mass was increased by about 3° C. and the mass was centrifuged. The xylitol purity of the mass was 56.5% of the dry matter. The crystals were separated with a centrifuge (basket diameter 22 cm, mesh size 0.15 mm) at 4500 rpm for 5 minutes and washed. The yield was 55 g of dried crystal. The xylitol purity of the crystals was 68.0% on dry matter basis.

EXAMPLE 22

Hydrogenation of Xylose

The raw material was a xylose fraction that was obtained as described in Example 1 and that had been subjected to conventional ion exchange.

The hydrogenation was carried out in a batch-type autoclave (Meclimex) in conditions where the pressure was 4000 kPa, the temperature was 100° C. and the dry solids content of the syrup was 47.8% by weight. The amount of the catalyst (Raney nickel, Chemcat J 10 GS™) was 10%, calculated on the dry matter of the syrup, of wet catalyst slurry. The reaction time was 90 minutes. The xylose and xylitol contents of the feed and product solutions are shown in Table 11.

TABLE 11

Hydrogenation of xylose

| | Xylose % dry matter | Xylonic acid % dry matter |
|---|---|---|
| Feed | 98.9 | 0 |
| Product | 0 | 98.6 |

We claim:

1. A method for producing xylitol from a cooking liquor from a sulphite cook or part thereof containing xylose and xylonic acid comprising separating said xylonic acid from said cooking liquor and reducing said separated xylonic acid to xylitol and recovering said xylitol.

2. A method according to claim 1, characterized in that it comprises a further step where xylose is also separated from the material containing xylose and xylonic acid.

3. A method according to claim 2, characterized in that the separated xylose is reduced to xylitol, and the xylitol is recovered.

4. A method according to claim 2, characterized in that the separated xylose is crystallized and recovered, and xylonic acid is reduced to xylitol.

5. A method according to claim 1, characterized in that the material containing xylose and xylonic acid is a cooking liquor from a magnesium sulphite cook.

6. A method according to claim 1, characterized in that the material containing xylose and xylonic acid is a cooking liquor from a calcium sulphite cook.

7. A method according to any one of claim 1 characterized in that the separation is carried out chromatographically, by extraction, crystallization or ion exchange.

8. A method according to any one claim 1 characterized in that the separation is carried out chromatographically.

9. A method according to claim 8, characterized in that the separation is carried out as a batchwise or continuous process.

10. A method according to claim 9, characterized in that it comprises the following steps:
   a) a cooking liquor from a magnesium sulphite cook is chromatographed by using a separation resin in magnesium form to obtain a fraction rich in xylose, a mixed fraction and a residual fraction in magnesium form, and
   b) the obtained fraction rich in xylose is chromatographed by using a separation resin that is in the form of magnesium or a monovalent metal, and a fraction concentrated with respect to xylose is recovered, and a fraction that is in salt form and that is concentrated with respect to xylonic acid is recovered.

11. A method according to claim 10, characterized in that the residual fraction in magnesium form obtained in step a) is returned to the preparation of the cooking acid of the magnesium sulphite cook.

12. A method according to claim 10, characterized in that the resin in steps a) and b) is a strongly acid cation-exchange resin.

13. A method according to claim 10, characterized in that the resin in step b) is in the form of a monovalent metal.

14. A method according to claim 13, characterized in that the monovalent metal is sodium.

15. A method according to claim 13, characterized in that it comprises a further step where the xylose-containing fraction obtained in step a) is softened before step b).

16. A method according to claim 15, characterized in that the decationization is carried out by using a cation-exchange resin in sodium form.

17. A method according to claim 15, characterized in that the softening is carried out by using a cation-exchange resin in hydrogen form.

18. A method according to claim 15, characterized in that the pH of the xylose-containing fraction obtained in the softening is adjusted to about 5.5.

19. A method according to claim 18, characterized in that the pH is adjusted with sodium hydroxide.

20. A method according to claim 15, characterized in that the residual fraction in salt form that is obtained in step b) is led through a cation exchanger in hydrogen form and the obtained acid is used to regenerate to hydrogen form the cation-exchange resin that is produced in the softening carried out before step b) and that is in magnesium form.

21. A method according to claim 20, characterized in that the resin in sodium form obtained after the cation exchange is regenerated with an acid and the obtained sodium salt is used to convert the softening column regenerated to hydrogen form into sodium form.

22. A method according to claim 21, characterized by using the acid that is obtained by converting the softening column regenerated to hydrogen form into sodium form.

23. A method according to claim 20, characterized in that the magnesium fraction formed in the regeneration of the cation-exchange resin used in the softening is returned to the preparation of the cooking acid of the magnesium sulphite cook.

24. A method according to claim 10, characterized in that the resin in step b) is in magnesium form.

25. A method according to claim 24, characterized in that the pH of the fraction rich in xylose and obtained in step a) is adjusted to 3.5 to 6.5.

26. A method according to claim 25, characterized in that the pH is adjusted to 5.5.

27. A method according to claim 25, characterized in that the pH is adjusted with MgO.

28. A method according to claim 11, characterized in that the magnesium xylonate obtained in step b) is crystallized.

29. A method according to claim 1, characterized in that the separation is carried out by extraction.

30. A method according to claim 29, characterized in that the extraction is carried out with ethanol.

31. A method according to claim 1, characterized in that the separation is carried out by ion exchange.

32. A method according to any one of claims 2, 3, 5–6, characterized in that the separated xylose is oxidized into xylonic acid before the reduction.

33. A method according to claim 1, characterized in that the reduction is carried out catalytically.

34. A method according to claim 33, characterized in that the catalyst is Ru, Pd, Pt, Raney-Ni or Rh.

35. A method according to claim 34, characterized in that the catalyst is Ru.

36. A method according to claim 33, characterized in that the reduction is carried out at 70 to 150° C.

37. A method according to claim 33, characterized in that the reduction is carried out at a pressure of 10 000 to 13 000 kPa.

38. A method according to claim 33, characterized in that the reduction of xylose is carried out at a pH of 5 to 7 and the reduction of xylonic acid is carried out at a pH of 1.5 to 2.5.

39. A method according to claim 1, characterized in that the reduction is carried out by using a metal hydride reagent.

40. A method according to claim 39, characterized in that the metal hydride reagent is sodium borohydride.

41. A method according to claim 1, characterized in that xylitol is separated from the product solution of the reduction chromatographically.

42. A method according to claim 1, characterized in that xylitol is separated from the product solution of the reduction by crystallization.

* * * * *

UNITED STATES PATENT AND TRADEMARK OFFICE
CERTIFICATE OF CORRECTION

PATENT NO. : 5,998,607  
DATED : December 7, 1999  
INVENTOR(S) : H. Heikkila et al.

Page 1 of 1

It is certified that error appears in the above-identified patent and that said Letters Patent is hereby corrected as shown below:

<u>Column 4,</u>
Line 6, "exchange The" should read -- exchange. The --

<u>Column 6,</u>
Line 10, "26.1" should read -- 28.1 --
Line 37, "Example 5" should be on line 57.
Line 62, "$SO_2/1$" should read -- $SO_2/1$ --

<u>Column 7,</u>
Line 31, "flatter" should read -- matter --

<u>Column 12,</u>
Line 60, "Meclimex" should read -- Medimex --

<u>Column 13,</u>
Line 5, "xylonic acid" should read -- xylitol --
Line 33, "any one claim 1" should read -- to claim 1 --

<u>Column 14,</u>
Line 32, "2,3,5-6" should read -- 2,3,6 or 7 --

Signed and Sealed this

Sixth Day of August, 2002

*Attest:*

JAMES E. ROGAN
*Director of the United States Patent and Trademark Office*

*Attesting Officer*